US00RE37159E

(19) United States
(12) Reissued Patent
Ohmoto et al.

(10) Patent Number: US RE37,159 E
(45) Date of Reissued Patent: May 1, 2001

(54) PROPANOL DERIVATIVES AND PERFUMES CONTAINING THE SAME

(75) Inventors: Tatsuya Ohmoto; Akemi Shimada, both of Kamakura; Takeshi Yamamoto, Kawasaki, all of (JP)

(73) Assignee: Takasago International Corporation, Tokyo (JP)

(21) Appl. No.: 09/111,180

(22) Filed: Jul. 8, 1998

Related U.S. Patent Documents

Reissue of:
(64) Patent No.: 5,250,512
Issued: Oct. 5, 1993
Appl. No.: 07/879,738
Filed: May 6, 1992

U.S. Applications:
(63) Continuation of application No. 07/592,099, filed on Oct. 3, 1990, now abandoned.

(30) Foreign Application Priority Data

May 17, 1990 (JP) ..... 2-125520

(51) Int. Cl.[7] ..... A61K 7/46
(52) U.S. Cl. ..... 512/22; 568/822
(58) Field of Search ..... 512/22; 568/822

(56) References Cited

U.S. PATENT DOCUMENTS 4,252,896 * 2/1981 Klein et al. ..... 568/822
4,623,750 * 11/1986 Schulte-Elte et al. ..... 568/822
4,626,381 * 12/1986 Schulte-Elte et al. ..... 568/822
4,626,602 * 12/1986 Schulte-Elte et al. ..... 568/822

FOREIGN PATENT DOCUMENTS

0233904 * 8/1988 (EP) ..... 512/22
0118809 * 9/1994 (EP) ..... 512/22
0118817 * 9/1994 (EP) ..... 512/22

OTHER PUBLICATIONS

Helv. Chim. Acta, vol. 68, pp. 1961–1985, 1984.*
Chemical Abstracts, vol. 101, No. 12, abstract 97504g, 1984.*

* cited by examiner

*Primary Examiner*—James H. Reamer
(74) *Attorney, Agent, or Firm*—Sughrue, Mion, Zinn, Macpeak & Seas, PLLC

(57) ABSTRACT

An optically active 3-[6(S)-2,2,6-trimethylcyclohexan-1-yl] propanol derivative represented by formula (I):

(I)

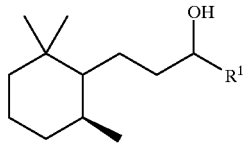

wherein $R^1$ represents a lower alkyl group, and a perfume containing the same as an active ingredient are disclosed.

14 Claims, No Drawings

PROPANOL DERIVATIVES AND PERFUMES CONTAINING THE SAME

Matter enclosed in heavy brackets [ ] appears in the original patent but forms no part of this reissue specification; matter printed in italics indicates the additions made by reissue.

This is a Continuation of Application No. 07/592,099 filed Oct. 3, 1990 abandoned.

FIELD OF THE INVENTION

This invention relates to a novel propanol derivative useful for perfume cosmetics, etc., and a perfume containing the same as an active ingredient.

BACKGROUND OF THE INVENTION

Some naturally-occurring compounds exhibit various characteristics attributed to their asymmetric structure. Of physiologically active substances having an asymmetric structure, many of those useful for humans are confined to the respective specific antipode. This tendency is particularly conspicuous in the field of pharmaceuticals, agricultural chemicals, pheromones, and food additives. It is known in these fields that a racemic mixture may have a markedly reduced effect or rather exhibit a counter effect. The field of perfumes is no exception to this tendency. For example, 1-menthol has the odor of mint; d-carvone has the odor of Caraway L.; and d-nootkatone has the odor of grapefruit. Each of these optical antipodes is different from or stronger than the respective other optical antipodes in odor. The latest examples of such a phenomenon are observed in α-ionine, hydroxycitronellal, and rose oxide. For the detail, reference can be made to Kaqaku Sosetsu, No. 14, Ch. 6 "Aji to Nioi no Kagaku" (1976).

Therefore, development of optically active perfume components as well as development of novel perfumes would lead to development of optical antipodes having a new odor or usefulness and are of industrial significance.

With respect to 3-(2,2,6-trimethylcyclohexan-1-yl) propanol derivatives, compounds known to have a wood-like fragrance or an amber-like fragrance include 1-(2,2,6-trimethylcyclohexan-1-yl)pentan-3-ol having an ethyl group as the alkyl moiety (see West German Patent Application (OLS) No. 2,455,761), 1-(2,2,6-trimethylcyclohexan-1-yl) hexan-3-ol having a propyl group as the alkyl moiety (see JP-A-62-70314, JP-B-1-38438, JP-B-59-18373, JP-A-61-191636, and JP-B-62-16935; the terms "JP-A" and "JP-B" as used herein mean an "unexamined published Japanese patent application" and an "examined Japanese patent publication", respectively), and 5-methyl-1-(2,2,6-trimethylcyclohexan-1-yl(hexan-3-ol having an isobutyl group as the alkyl moiety (See USSR Patent 1,082,780).

JP-B-1-38438 discloses a composition of 1-(2,2,6-trimethylcyclohexan-1-yl)hexan-3-ol comprising 80% or more of a trans isomer and not more than 20% of a cis isomer.

Since these cis and trans isomers each has an asymmetric carbon atom in the molecule thereof, it is expected that there are a pair of enantiomers, i.e., (+)-isomer and (−)-isomer. However, the compounds disclosed in the above-cited references exist as a racemic mixture. No other study has been reported on synthesis or properties of the individual optical isomers.

The recent diversity of cosmetics and sanitary goods has created a new increasing demand for a perfume material which has a high diffusibility, unique scent, high tastiness, high retention, satisfactory stability, and high safety. In particular, perfume materials having an amber-like fragrance and satisfying these requirements have been wanted.

SUMMARY OF THE INVENTION

Accordingly, an object of this invention is to provide an optically active compound which is capable of imparting an amber-like fragrance while meeting the above-described demand.

Another object of this invention is to provide a perfume comprising the above-described optically active compound as an active ingredient.

In the light of the above-mentioned circumstances, the inventors have conducted extensive investigations and, as a result, succeeded to synthesize an optically active isomer of a 3-(2,2,6-trimethylcyclohexan-1-yl)propanol derivative and found that the 6(S)-isomer of the compound has a sharp and highly diffusible amber fragrance free from a wood-like fragrance accompanied by the dim odor of mold and is useful as a perfume. The present invention has been completed based on this finding.

The present invention relates to an optically active 3-[6(S)-2,2,6-trimethylcyclohexan-1-yl]propanol derivative represented by formula (I):

(I)

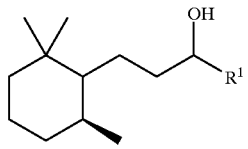

wherein $R^1$ represents a lower alkyl group.

The present invention further relates to a perfume containing the optically active compound of formula (I) as an active ingredient.

DETAILED DESCRIPTION OF THE INVENTION

In formula (I), the lower alkyl group as represented by $R^1$ preferably contains from 1 to 4 carbon atoms, and specific examples thereof include a methyl group, and ethyl group, an n-propyl group, an isopropyl group, an n-butyl group, and an isobutyl group.

The optically active 3-[6(S)-2,2,6-trimethylcyclohexan-1-yl]propanol derivative of formula (I) can be synthesized, for example, in the following reaction scheme.

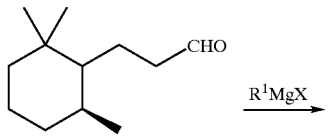

(2)

-continued

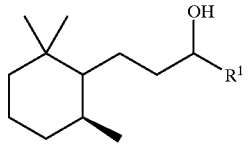

(1)

wherein $R^1$ is as defined above; and X represents a halogen atom.

*The above active optically active propanol derivatives of formula (I) can also be represented by the following formula (A):*

(A)

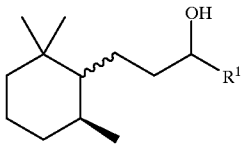

*In the above formula (A), the wavy line means a bond whose direction is not specified in the formula. It thus includes both the trans and cis forms of the compounds of formula (I) as reflected in Synthesis Examples 7–17.*

That is, the optically active 3-[6(S)-2,2,6-trimethylcyclohexan-1-yl]propanol derivative of formula (I) can easily be synthesized by reacting an optically active 3-[6(S)-2,2,6-trimethylcyclohexan-1-yl]propanal represented by formula (2) with an alkylmagnesium halide represented by the formula, $R_1MgX$, wherein $R^1$ and X are the same as defined above.

The starting compound, 3-[6(S)-2,2,6-trimethylcyclohexan-1-yl]propanal (2), is a novel compound and can be synthesized in the following reaction scheme:

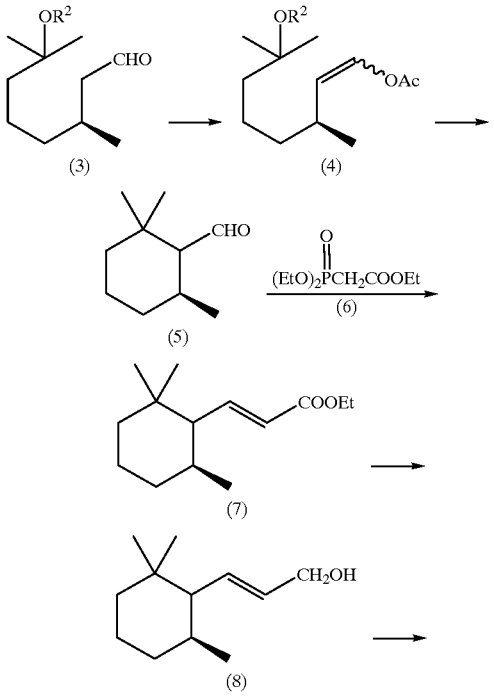

-continued

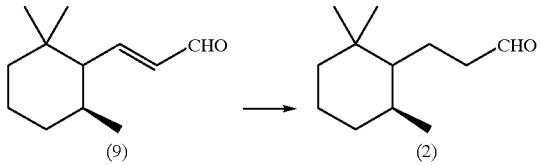

(9) (2)

wherein $R^2$ represented a hydrogen atom or a methyl group; Ac represents an acetyl group; Et represents an ethyl group; and the wavy line indicates a trans- and/or cis-position.

While an optically active 1-[6(S)-2,2,6-trimethylcyclohexan]carbaldehyde (5) as an intermediate compound of the above reaction route is known to by synthesized by starting with optically active citronellal as described in JP-A-63-44544, it can easily be synthesized in a high yield by starting with optically active 1-methoxycitronellal (3) which is used on an industrial scale as a perfume or juvenile pheromone of mosquito larvae. Namely, 1-methoxycitronellal (3) is reacted with acetic anhydride to obtain an enol acetate (4) which, as produced, is then subjected to cyclization in the presence of a phosphoric acid catalyst to obtain the compound (5).

The compound (5) is then reacted with triethyl phosphonoacetate (6) by utilizing the Wittig reaction described, e.g., In Herbert O. House, Modern Synthetic Reaction, p. 690, W. A. Benjamin, Inc., Menlo Park, Calif., U.S.A. (1972) by synthesize optically active ethyl 3-[6(S)-2,2,6-trimethylcyclohexan-1yl]acrylate (7).

The compound (7) is reduced by using sodium borohydride or sodium bis(2-methoxyethoxy)aluminum hydride to synthesize optically active 3-[6(S)-2,2,6-trimethylcyclohexan-1-yl]-2-propen-1-ol (8) which is then oxidized with manganese dioxide to obtain optically active 3-[6(S)-2,2,6-trimethylcyclohexan-1-yl]-2-propen-1-al (9). The compound (9) is then hydrogenated in the presence of a palladium-on-carbon as a catalyst to synthesize optically active 3-[6(S)-2,2,6-trimethylcyclohexan-1-yl]propanal (2).

While the above description relates to synthesis of the 6(S)-compound, a 6(R)-compound can be obtained in the similar manner by starting with d-methoxycitronellal in place of 1-methoxycitronellal.

It surprisingly turned out that the scent given off by the thus obtained 3-[2,2,6-trimethylcyclohexan-1-yl]propanol derivatives utterly differs between different optical antipodes. More specifically, the 6(S)-compounds have a sharp amber fragrance with very high diffusibility in common, though somewhat different in strength and quality depending on the kind of $R^1$. On the other hand, the 6(R)-compounds basically produce no amber fragrance and give off a powerless wood-like fragrance with a little moldiness. The racemates give off a dull woody amber fragrance which is remarkably different from and far less powerful than that of the 6(S)-compounds.

Further, each of the 6(S)-compounds differing in $R^1$ was proved effective to impart to a perfume composition a distinct top note to yield a fresher and tastier composition as though it is of different kind from the corresponding 6(R)-compound or racemate. It was also proved that the 6(S)-compounds have high fragrance retention and high masking effects over odors of bases of soaps, etc., odors of bleaching agents, and ozone odor and are, therefore, very useful as perfume materials.

Thus, there is provided a fresh and tasty fragrance or a fragrance modifying or strengthening agent with high diffusibility and retention, which contains the 3-[6(S)-2,2,6-trimethylcyclohexan-1-yl]propanol derivative according to the present invention. There are also provided cosmetics, sanitary goods, pharmaceuticals, etc., which contains the compound of the invention as a perfume component. That is, the compound according to the present invention can be incorporated in an amount effective to impart its unique fragrance into bases of hair care cosmetics, e.g., shampoos, rinses, perfumes, colognes, hair tonics, hair creams, pomades, etc.; bases of facial cosmetics, e.g., face powders, lip sticks, etc.; toilet foods, e.g., face cleansers, soaps, disinfectants, tooth pastes, mouth-washes, toilet paper, etc.; various detergents, e.g., dish washing detergents, laundry detergents, textile softeners, disinfectant detergents, deodorant detergents, bleaching agent, etc.; environmental aromatizers, furniture care goods, insecticides; flavors for facilitating administration of medicines; and the like thereby to enhance the commercial value of these goods.

A suitable amount of the propanol derivative according to the present invention which is used in a perfume composition to be applied to various products is from 0.0001 to 50% by weight and preferably from 0.001 to 20% by weight.

The present invention is now illustrated in greater detail with reference to Synthesis Examples and Examples. All the parts, percents, and ratios are by weight unless otherwise indicated.

SYNTHESIS EXAMPLE 1

Synthesis of 1-[6(S)-2,2,6-Trimethylcyclohexan] carbaldehyde (5)

In a 5 l-volume four-necked flask equipped with a condenser, a thermometer, a dropping funnel, and a stirrer were charged 871 g of acetic anhydride, 27 g of sodium acetate, and 706 g of triethylamine under a nitrogen atmosphere, and the mixture was heated to 75° C. while stirring. To the resulting solution was added dropwise 1 kg of 1-methoxycitronellal (a commercially available product of Takasago International Corporation; $[\alpha]_D^{25}$: −10.42°; optical purity: 98% ee) over 1 hour.

After the dropwise addition, the reaction mixture was refluxed at 101° to 117° C. for 6-hours, followed by cooling to 5° C. To the reaction mixture were added 500 g of water and 500 g of toluene to conduct water washing and liquid-liquid separation. Again, 500 g of water was added thereto to conduct water washing and liquid-liquid separation to obtain 1,690 g of a toluene solution of an enol acetate (4). Gas chromatography ("HEWLETT PACKARD 5890"; column; Carbowax 20M (HP); 0.2 mm ID×25 m) (hereinafter abbreviated as GC) revealed that the solute was composed of 29.5% of cis-compound (4), 62.75% of trans-compound (4), and 5.3% of diacetate (10).

(4)-Trans

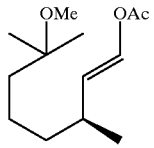

(4)-Cis

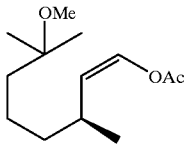

-continued (10)

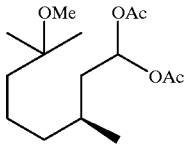

wherein Me represents a methyl group; and Ac represents an acetyl group. Spectral Data: Mass (CI)

| | |
|---|---|
| (4)-Trans: | 229 (M + 1,1), 197 (70), 155 (42), 137 (100), 95 (12), 73 (41) |
| (4)-Cis: | 229 (M + 1,3), 197 (100), 155 (88), 137 (98), 95 (24), 73 (82) |
| (10): | 289 (M + 1,0.2), 197 (85), 155 (75), 137 (100), 103 (19), 73 (33) |

In a 5 l-volume four-necked flask equipped with a condenser, a thermometer, an outlet for water, and a stirrer were charged 1,690 g of the resulting toluene solution of compound (4), 620 g of 85% phosphoric acid, and 500 g of toluene, and the mixture was heat-refluxed at 71° to 107° C. for 3 hours with stirring under a nitrogen atmosphere while controlling the refluxing temperature by removing the produced methanol together with toluene in small portions.

The reaction mixture was cooled to 5° C. and washed with 2,000 ml of cold water, followed by water washing and liquid-liquid separation. The mixture was further washed and separated successively with 2,000 ml of water, 2,000 ml of a 5% soda ash aqueous solution, and 2,000 ml of a saturated sodium chloride aqueous solution. The toluene was removed by distillation under reduced pressure to obtain 872 g of a concentrated oil. The resulting concentrated oil was subjected to rectification using a 1 mm distillation column packed with Helipack to obtain 425 g of optically active 1-[6(S)-2,2,6-trimethylcyclohexan]carbaldehyde (5).

Boiling point: 80°–81° C./8 mmHg $[\alpha]_D^{25}$: −0.47°

Purity by GC: (5)-Trans: 90%; (5)-Cis: 10%

(5)-Trans

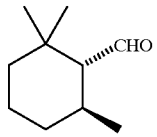

(5)-Cis

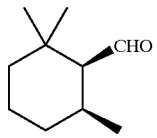

SYNTHESIS EXAMPLE 2

Synthesis of Ethyl 3-[6(S)-2,2,6-trimethylcyclohexan-1-yl]acrylate (7)

In a 10 l-volume four-necked flash equipped with a condenser, a thermometer, a dropping funnel, and a stirrer were charged 1,000 g of a sodium hydride dispersion (purity: 60% and 3,400 ml of tetrahydrofuran, and 565 g of triethyl phosphonoacetate (6) was added dropwise thereto over 1 hours. The mixture was stirred for 1 hour until hydrogen gas was not evolved.

Then, 424 g of the compound (5) prepared in Synthesis Example 1 was added dropwise thereto at room temperature over 1 hour, followed by stirring at room temperature for 3 hours to complete the reaction. To the reaction mixture was added 1 kg of water to conduct water washing and liquid-liquid separation, followed by working up in a usual manner to obtain 526 g of a concentrated oil.

The resulting concentrated oil was subjected to rectification using a 30 cm Helipack-packed distillation column to obtain 465 g of optically active ethyl 3-[6(S)-2,2,6-trimethylcyclohexan-1-yl]acrylate (7).

Boiling point: 108–109° C./0.95.mmHg $[\alpha]_D^{25}$: +21.41°

Purity by GC: 99.5% (the product was not separated into the cis and trans compounds.)

Spectral Data of Compound (7):

$^1$HNMR (400 MHz, $CDCl_3$, δ): 0.75 (3H, d, J=4.3 Hz), 0.82 (3H, s), 0.88 (3H, s), 1.29 (3H, t, J=7.1 Hz), 0.89–1.8 (8H), 4.18 (2H, q, J=7.1 Hz), 5.76 (1H, d, J=15.5 Hz), 6.73 (1H, q, J=15.5 Hz, J=10.1 Hz)

MS m/e: 224 ($M^+$, 18), 209 (7), 179 (25 ), 168 (9), 150 (37), 136 (100), 125 (23), 109 (50), 95 (75), 81 (64), 69 (70), 55 (35), 41 (16), 29 (11)

IR $\nu_{max}$ ($cm^{-1}$): 2925, 1720, 1650, 1365, 1150–1180

SYNTHESIS EXAMPLE 3

Synthesis of 3-[6(S)-2,2,6-Trimethylcyclohexan-1-yl]-2-propen-1-ol (8)

Into a 5 l-volume four-necked flask equipped with a condenser, a thermometer, a dropping funnel, and a stirrer were charged 633 g of a 70% toluene solution of sodium bis(2-methoxyethoxy)aluminum hydride and 2,100 ml of toluene under a nitrogen atmosphere, and 460 g of the compound (7) prepared in Synthesis Example 2 was added dropwise to the mixture at room temperature over 2 hours, followed by stirring at that temperature for 1 hour to complete the reaction.

The reaction mixture was worked up in a usual manner to obtain 390 g of a concentrated oil which was then purified by rectification using a 30 cm Helipack-packed distillation column to obtain 322 g of optically active 3-[6(S)-2,2,6-trimethylcyclohexan-1-yl]-2-propen-1-ol (8).

Boiling point: 95°–96° C./0.95 mmHg $[\alpha]_D^{25}$: +23.33°

Purity by GC: (8)-Trans: 95%; (8)-Cis: 5%

(8)-Trans

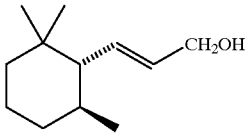

-continued (8)-Cis

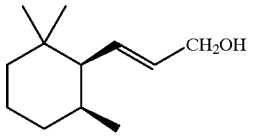

Spectral Data of (8)-Trans:

$^1$H-NMR (400 MHz, $CDC_3$, δ): .76 (3H, d, J=6.3 Hz), 0.82 (6H, s), 0.87–1.49 (8H), 1.69 (1H, m), 4.11 (2H, q, Jgem=1.3 Hz, Jvic=5.9 Hz), 5.39 (1H, m), 5.57 (1H, m)

MS m/e: 182 ($M^+$, 2), 164 (4), 149 (18), 138 (12), 124 (39), 109 (52), 95 (70), 81 (63), 69 (100), 55 (57), 41 (22), 28 (6)

IR $\nu_{max}$($cm^{-1}$): 3325, 2920, 1365, 970

Spectral Data of (8)-Cis:

MS m/e: 182 ($M^{30}$, 3), 164 (7), 149 (18), 138 (11), 124 (48), 109 (74), 95 (78), 81 (50), 69 (100), 55 (46), 41 (24), 32 (9.6)

SYNTHESIS EXAMPLE 4

Synthesis of 3-[6(S)-2,2,6-Trimethylcyclohexan-1-yl]-2-propen-1-al (9)

In a 2 l-volume four-necked flask equipped with a thermometer and a stirrer were charged 4,300 g of activated manganese dioxide, 10 l of n-octane, and 320 g of the compound (8) synthesized in Synthesis Example 3, and the mixture was stirred at 40° to 45° C. for 12 hours to complete the reaction. The reaction mixture was filtered and concentrated to obtain 326 g of a concentrated oil which was then purified by rectification by using a 30 cm Helipack-packed distillation column to obtain 277 g of optically active 3-[6(S)-2,2,6-trimethylcyclohexan-1-yl]-2-propen-1-al (9).

Boiling point: 90°–91° C./0.9 mmHg $[\alpha]_D^{25}$: +33.44°

Purity by GC: (9)-Trans: 95.5%; (9)-Cis: 4.5%

(9)-Trans

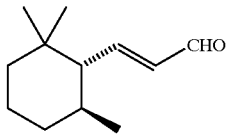

(9)-Cis

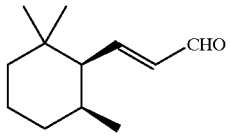

Spectral Data of (9)-Trans:

$^1$H-NMR (400 MHz, $CDCl_3$, δ): 0.76 (3H, d, J=2.4 Hz), 0.91 (3H, s), 0.84 (3H, s), 1.22–1.71 (8H), 6.08 (1H, q, J=15.5 Hz, J=8 Hz), 6.61 (1H, q, J=15.5Hz, J=10.1Hz), 9.52 (1H, d, J=8Hz)

MS m/e: 180 ($M^+$, 13), 165(11), 147 (6), 137 (43), 123 (31), 109 (41) 95 (100) 81 (72) 69 (35) 55 (30), 41 (24 )

IR $\nu_{max}$ ($cm^{-1}$): 2920, 2860, 2840, 1680, 1460, 1370, 1120, 1110

Spectral Data of (9)-Cis:

MS m/e: 180 ($M^+$, 11), 165 (11), 147 (4), 137 (43), 123 (33), 109 (31), 95 (100), 81 (51), 69 (26), 55 (26), 41 (20)

SYNTHESIS EXAMPLE 5

Synthesis of 3-[6(S)-2,2,6-Trimethylcyclohexan-1-yl]propanal (2)

In 7 l of ethanol was added 276 g of the compound (9) synthesized in Synthesis Example 4, and the mixture was subjected to hydrogenation at room temperature at atmospheric pressure using 14 g of 5% paladium-on-carbon as a catalyst. After the reaction, the catalyst was removed by filtration, and the resulting 290 g of a concentrated oil was purified by rectification using a 30 cm Helipack-packed distillation column to obtain 242 g of optically active 3-[6(S)-2,2,6-trimethylcyclohexan-1-yl]propanal (2).

Boiling point: 93°–94° C./1.1 mmHg $[\alpha]_D^{25}$: +11.88°

Purity by GC: (2)-Trans: 95.7%; (2)-Cis: 4.3%

(2)-Trans

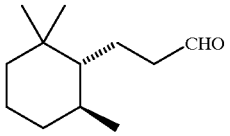

(2):Cis

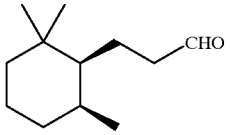

Spectral Data of (2)-Trans:

$^1$HNMR (400 MHz, $CDCl_3$, δ): 0.80 (3H, d, J=4.3 Hz), 0.90 (6H), 0.92–1.78 (8H), 2.27–2.53 (4H), 9.74 (1H, t, J=1.9 Hz)

MS m/e 182 ($M^+$, 8), 167 (12), 149 (16), 138 (17), 123 (13), 109 (35), 95 (17), 82 (70), 69 (100), 55 (48), 41 (20)

IR $\nu_{max}$ ($cm^{-1}$): 2920, 2890, 2840, 1720, 1460, 1390, 1380

Spectral Data of (2)-Cis:

MS m/e: 182 ($M^+$, 4), 167 (7), 149 (16), 138 (52), 123 (68), 109 (41), 95 (76), 82 (98), 69 (100), 55 (52), 41 (18), 29 (41), 18 (9)

SYNTHESIS EXAMPLE 6

Synthesis of 3-[6(R)-2,2,6-Trimethylcyclohexan-1-yl]propanal (11)

The same procedures as in Synthesis Examples 1 through 5 were repeated, except for replacing the starting 1-methoxycirtonellal with d-methoxycitronellal (a commercially available product sold by Takasago International Corporation; $[\alpha]_D^{25}$: +10.42°; optical purity: 98% ee), to obtain 240 g of optically active 3-[6(R)-2,2,6-trimethylcyclohexan-1-yl]propanal (11).

Boiling point: 93–94° C./1.1 mmHg $[\alpha]_D^{25}$–11.87°

Purity by GC: (11)-Trans: 95.6%; (11)-Cis: 4.4%

(11)-Trans

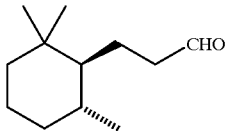

(11)-Cis

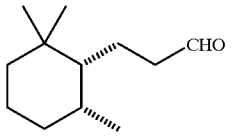

SYNTHESIS EXAMPLE 7

Synthesis of 1-[6(S)-2,2,6-Trimethylcyclohexan-1-yl]butan-3-ol (12)

In a 300 ml-volume four-necked flask equipped with a condenser, a thermometer, a dropping funnel, a gas blowing tube, and a stirrer were charged 5.0 g of a magnesium powder, 0.001 g of iodine, 0.5 g of methyl iodide, and 10 ml of tetrahydrofuran under a nitrogen atmosphere. After confirming the start of a Grignard reaction (generation of bubbling), of tetrahydrofuran was added thereto, and methyl chloride gas was blown into the reaction mixture at 40° to 45° C. for 4 hours with stirring until the magnesium powder disappeared to thereby prepare a tetrahydrofuran solution of methylmagnesium chloride. To the resulting solution was added dropwise a solution of 15 g of the 3-[6(S)-2,2,6-trimethylcyclohexan-1-yl]propanal (2) obtained in Synthesis Example 5 in 15 ml of tetrahydrofuran at 5° C. over 2 hours, followed by stirring at that temperature for 4 hours to complete the reaction. The reaction mixture was worked up in a usual manner, and 17 g of the resulting concentrated oil was subjected to rectification using a 20 cm Helipack-packed distillation column to obtain 13 g of optically active 1-[6(S)-2,2,6-trimethylcyclohexan-1-yl]butan-3-ol (12).

Boiling point: 93°–95° C./1 mmHg $[\alpha]_D^{25}$: +12.98°Purity by GC: (12)-Trans: 95.3%; (12)-Cis: 4.7%

Elemental analysis:

Calcd. (%) C: 78.72; H: 13.21; O: 8.07

Found (%) C: 78.71; H: 13.22; O: 8.07

(12)-Trans

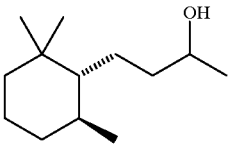

(12)-Cis

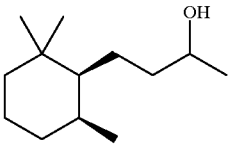

Spectral Data of (12)-Trans:

$^1$HNMR (400 MHz, $CDCl_3$, δ): 3.75 (1H, m), 1.19 (3H, d, J=6.17 Hz), 0.88 (3H, d, J=6 Hz), 0.89 (3H, s), 0.79 (3H, s), 0.55 (1H, m), 1.6–0.9 (12H, m)

MS m/e: 198 ($M^+$, 1), 180 (8), 165 (13), 151 (1), 138 (13), 124 (40), 109 (65), 95 (59), 82 (53), 69 (100), 55 (49), 45 (27), 29 (1)

IR $\nu_{max}$ ($cm^{-1}$): 3348, 1460, 1375, 1100

Spectral Data of (12)-Cis:

MS m/e: 198 (0), 180 (4), 165 (24), 138 (20), 123 (39), 109 (59), 95 (61), 82 (67), 69 (100), 55 (59), 43 (30), 32 (5)

SYNTHESIS EXAMPLE 8

Synthesis of 1-[6(R)-2,2,6-Trimethylcyclohexan-1-yl]butan-3-ol (13)

The same procedure as in Synthesis Example 7 was repeated, except for replacing the starting 3-[6(S)-2,2,6-trimethylcyclohexan-1-yl]propanal with 10 g of 3-[6(R)-2,2,6-trimethylcyclohexan-1-yl]propanal, to obtain 9 g of optically active 1-[6(R)-2,2,6-trimethylcyclohexan-1-yl]butan-3-ol (13).

Boiling point 93°–95° C./1 mmHg $[\alpha]_D^{25}$: −12.96°

Purity by GC: (13)-Trans: 95.2%; (13)-Cis: 4.8

Elemental Analysis:

Calcd. (%) C: 79.57; H: 13.36; O: 7.07

Found (%) C: 79.54; H: 13.37; O: 7.09

(13)-Trans

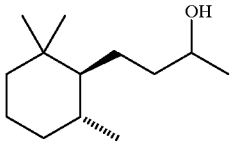

(13)-Cis

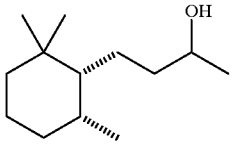

SYNTHESIS EXAMPLE 9

Synthesis of 1-[6(S)-2,2,6-Trimethylcyclohexan-1-yl]pentan-3-ol (14)

The same procedure as in Synthesis Example 7 was repeated, except for replacing the methyl iodide and methyl chloride gas with ethyl iodide and ethyl chloride gas, respectively to prepare a tetrahydrofuran solution of ethylmagnesium chloride. The resulting concentrated oil (17 g) was subjected to rectification by using a 20 cm Helipack-packed distillation column to obtain 13 g of optically active 1-[6(S)-2,2,6-trimethylcyclohexan-1-yl]pentan-3-ol (14).

Boiling point: 95°–97° C./1 mmHg $[\alpha]_D^{25}$: +13.08°

Purity by GC: (14)-Trans: 95.0%; (14)-Cis: 5.0%

Elemental Analysis:

Calcd. (%) C: 79.18; H: 13.29; O: 7.53

Found (%) C: 79.12; H: 13.32; O: 7.56

(14)-Trans

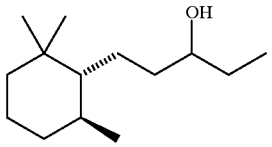

(14)-Cis

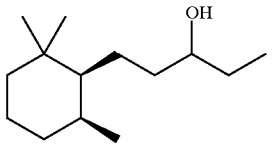

Spectral Data of (14)-Trans:

$^1$HNMR (400 MHz, $CDCl_3$, δ): 0.54 (1H, m), 0.79 (3H, s), 0.88–0.96 (10H), 1.00–1.66 (13H), 3.48 (1H, m)

MS m/e: 194 (M-18, 16), 179 (17), 165 (4), 151 (4), 138 (46), 124 (56), 109 (87), 95 (59), 82 (56), 69 (100), 55 (41), 41 (13), 31 (3), 82 (56), 69 (100), 55 (41), 41 (13), 31 (3)

IR $\nu_{max}$ ($cm^{-1}$): 3340, 2920, 2865, 2840, 1460, 1387, 1367

Spectral Data of (14)-Cis:

MS m/e: 194 (M-18), 179 (55), 165 (4), 151 (6), 138 (45), 123 (80), 109 (91), 95 (76), 82 (7), 69 (100), 55 (41), 41 (12), 31 (4)

SYNTHESIS EXAMPLE 10

Synthesis of 1-[6(R)-2,2,6-Trimethylcyclohexan-1-yl]pentan-3-ol (15)

The same procedure as in Synthesis Example 7 was repeated, except for replacing the methyl iodide and methyl chloride gas with ethyl iodide and ethyl chloride gas, respectively to prepare a tetrahydrofuran solution of ethylmagnesium chloride and replacing 15 g of the starting 3-[6(S)-2,2,6-trimethylcyclohexan-1-yl]propanal with 10 g of 3-[6(R)-2,2,6-trimethylcyclohexan-1-yl]propanal, to obtain 9 g of optically active 1-[6(R)-2,2,6-trimethylcyclohexan-1-yl]pentan-3-ol (15).

Boiling point: 95°–97° C./1 mmHg $[\alpha]_D^{25}$: −13.08°

Purity by GC: (15)-Trans: 95.0%; (15)-Cis: 5.0%

Elemental Analysis:

Calcd. (%) C: 79.18; H: 13.29; O: 7.53

Found (%) C: 79.15; H: 13.30; O: 7.55

(15)-Trans

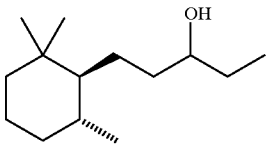

(15)-Cis

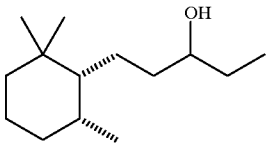

SYNTHESIS EXAMPLE 11

Synthesis of 1-[6(S)-2,2,6-Trimethylcyclohexan-1-yl]hexan-3-ol (16)

In a 300 ml-volume four-necked flask equipped with a condenser, a thermometer, a dropping funnel, and a stirrer were charged 5.0 g of a magnesium powder, 0.001 g of iodine, 0.5 g of n-propyl iodide, and 10 ml of tetrahydrofuran under a nitrogen atmosphere. After confirming the start of a Grignard reaction (bubbling and heat evolution), 100 ml of tetrahydrofuran was added to the reaction mixture, and 18 g of n-propyl chloride was added dropwise thereto at 35° to 40° C. over hours, followed by stirring at that temperature until the magnesium powder disappeared, to prepare a tetrahydrofuran solution of n-propylmagnesium chloride. To the resulting solution was added dropwise a solution of 15 g of the 3-[6(S)-2,2,6-trimethylcyclohexan-1-yl]propanal (2) obtained in Synthesis Example 5 in 15 ml of tetrahydrofuran at 5° C. over 2 hours, followed by stirring at that temperature for 4 hours to complete the reaction. The reaction mixture was worked up in a usual manner, and the resulting concentrated oil (18 g) was subjected to rectification by using a 20 cm Helipack-packed distillation column to obtain 13 g of optically active 1-[6(S)-2,2,6-trimethylcyclohexan-1-yl]hexan-3-ol (16).

Boiling point: 98°–101° C./1 mmHg $[\alpha]_D^{25}$: +11.98°

Purity by GC: (16)-Trans: 95.2%; (16)-Cis: 4.8%

Elemental Analysis:

Calcd. (%) C: 79.57; H: 13.36; O: 7.07

Found (%) C: 79.61; H: 13.33; O: 7.06

(16)-Trans

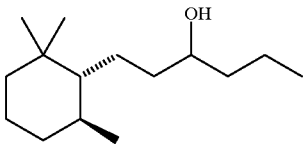

-continued (16)-Cis

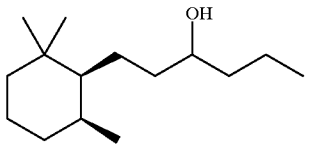

Spectral Data of (16)-Trans:

$^1$HNMR (400 MHz, $CDCl_3$, δ): 0.54 (1H, m), 0.79 (3H, s), 0.87–0.95 (9H), 0.97–1.27 (3H), 1.28–1.65 (13H), 3.56 (1H, m)

MS m/e: 208 (M-18), 193 (19), 183 (11), 165 (9), 152 (13), 138 (46), 124 (61), 109 (87), 95 (65), 82 (67), 69 (100), 55 (59), 43 (17)

IR $\nu_{max}$ ($cm^{-1}$): 3340, 2958, 2920, 2870, 2840, 1466, 1460, 1387, 1378, 1368

Spectral Data of (16)-Cis:

MS m/e: 208 (17), 193 (61), 183 (4), 165 (7), 152 (8), 138 (55), 109 (93), 95 (76), 82 (81), 69 (100), 55 (61), 41 (18)

SYNTHESIS EXAMPLE 12

Synthesis of 1-[6(R)-2,2,6-Trimethylcyclohexan-1-yl]hexan-3-ol (17)

The same procedure as in Synthesis Example 11 was repeated, except for replacing 15 g of the starting 3-[6(S)-2,2,6-trimethylcyclohexan-1-yl]propanal with 10 g of 3-[6(R)-2,2,6-trimethylcyclohexan-1-yl]propanal, to obtain 9 g of optically active 1-[6(R)-2,2,6-trimethylcyclohexan-1-yl]hexan-3-ol (17).

Boiling point: 98°–101° C./1 mmHg $[\alpha]_D^{25}$: 11.97°

Purity by GC: (17)-Trans: 95.1%; (17)-Cis: 4.9%

Elemental Analysis:

Calcd. (%) C: 79.57; H: 13.36; O: 7.07

Found (%) C: 79.54; H: 13.37; O: 7.09

(17)-Trans

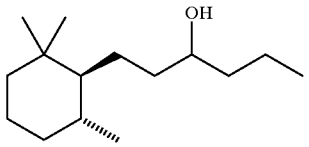

(17)-Cis

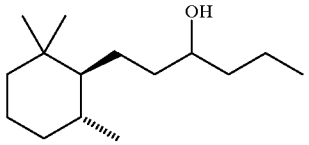

SYNTHESIS EXAMPLE 13

Synthesis of 1-[6(S)-2,2,6-Trimethylcyclohexan-1-yl]-4-methylpentan-3-ol (18)

The same procedure as in Synthesis Example 11 was repeated; except for replacing the n-propyl iodide with isopropyl iodide and dropwise adding isopropyl chloride in place of the n-propyl chloride over 3 hours to prepare a tetrahydrofuran solution of isopropylmagnesium chloride. The resulting concentrated oil (17 g) was subjected to rectification by using a 20 cm Helipack-packed distillation column to obtain 13 g of optically active 1-[6(S)-2,2,6-trimethylcyclohexan-1-yl]-4-methylpentan-3-ol (18).

Boiling point: 96°–97° C./1 mmHg $[\alpha]_D^{25}$: 13.71°

Purity by GC: (18)-Trans 95.1%; (18)-Cis: 4.9

Elemental Analysis:

Calcd. (%) C: 79.57; H: 13.36; O: 7.07

Found (%) C: 79.57; H: 13.36; O: 7.07

(18)-Trans

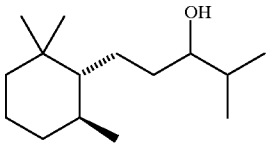

(18)-Cis

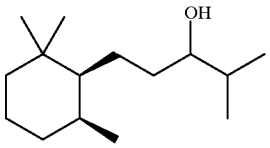

Spectral Data of (18)-Trans:

$^1$HNMR (400 MHz, $CDCl_3$, δ): 0.54 (1, m), 0.79 (3H, s), 0.87–0.94 (13H), 1.00–1.70 (12H), 3.3 (1H, m)

MS m/e: 236 ($M^+$, 4), 208 (7), 193 (7), 183 (28), 165 (10), 154 (3), 138 (22), 124 (33), 109 (73), 95 (59), 83 (67), 69 (100), 55 (33), 43 (15)

IR $\nu_{max}$ ($cm^{-1}$): 3350, 2950, 2920, 2865, 2840, 1468, 1387, 1368

Spectral Data of (18)-Cis:

MS m/e: 208 (14), 193 (36), 183 (11), 165 (8), 152 (3), 138 (33), 123 (57), 109 (74), 95 (65), 83 (77), 69 (100), 55 (35), 43 (16)

SYNTHESIS EXAMPLE 14

Synthesis of 1-[6(R)-2,2,6-Trimethylcyclohexan-1-yl]-4-methylpentan-3-ol (19)

The same procedure as in Synthesis Example 11 was repeated, except for using isopropyl iodide in place of the n-propyl iodide and adding dropwise isopropyl chloride in place of the n-propyl chloride over 3 hours to prepare a tetrahydrofuran solution of isopropylmagnesium chloride and replacing 15 g of the starting 3-[6(S)-2,2,6-trimethylcyclohexan-1-yl]propanal with 10 g of 3-[6(R)-2,2,6-trimethylcyclohexan-1-yl]propanal, to obtain 9 g of optically active 1-[6(R)-2,2,6-trimethylcyclohexan-1-yl]-4-methylpentan-3-ol (19).

Boiling point: 96°–97° C./1 mmHg $[\alpha]_D^{25}$: −13.70°

Purity by GC: (19)-Trans: 95.2%; (19)-Cis: 4.8%

Elemental Analysis:

Calcd. (%) C: 79.57; H: 13.36; O: 7.07

Found (%) C: 79.56; H: 13.37; O: 7.07

(19)-Trans

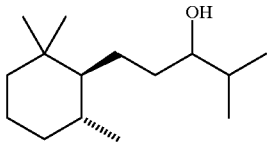

(19)-Cis

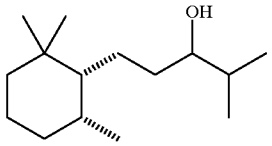

SYNTHESIS EXAMPLE 15

Synthesis of 1-[6(S)-2,2,6-Trimethylcyclohexan-1-yl]heptan-3-ol (20)

The same procedure as in Synthesis Example 11 was repeated, except for using n-butyl iodide in place of the n-propyl iodide and using 20 g of n-butyl chloride in place of g of the n-propyl chloride to prepare a tetrahydrofuran solution of n-butylmagnesium chloride. The resulting concentrated oil (19 g) was subjected to rectification by using a 20 cm Helipack-packed distillation column to obtain 13 g of optically active 1-[6(S)-2,2,6-trimethylcyclohexan-1-yl]heptan-3-ol (20).

Boiling point: 109°–110° C./1 mmHg $[\alpha]_D^{25}$: +11.23°

Purity by GC: (20)-Trans 95.2%; (20)-Cis: 4.8%

Elemental Analysis:

Calcd. (%) C: 79.93; H: 13.42; O: 6.65

Found (%) C: 79.95; H: 13.41; O: 6.64

(20)-Trans

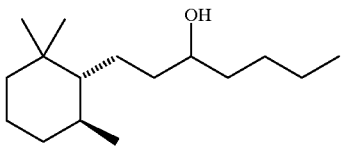

(20)-Cis

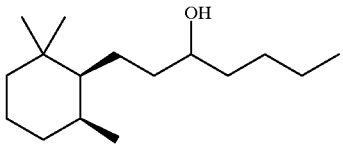

Spectral Data of (20)-Trans:

$^1$HNMR (400 MHz, $CDCl_3$, δ): 0.54 (1H, m), 0.79 (3H, s), 0.88–0.93 (10H), 1.00–1.24 (2H), 1.31–1.64 (16H), 3.5 (1H, m)

MS m/e: 222 (M-18, 13), 207 (13), 183 (7), 166 (10), 154 (5), 138 (32), 124 (41), 109 (57), 95 (46), 82 (43), 69 (100), 55 (19), 41 (7)

IR $\nu_{max}$ ($cm^{-1}$): 3340, 2918, 2865, 2840, 1468, 1460 1389, 1378, 1369

Spectral Data of (20-Cis:

MS m/e: 222 (M-18, 15), 207 (50), 183 (4), 166 (4), 151 (4), 138 (36), 123 (63), 109 (63), 95 (62), 82 (56), 69 (100), 55 (22), 41 (10)

SYNTHESIS EXAMPLE 16

Synthesis of 1-[6(R)-2,2,6-Trimethylcyclohexan-1-yl]heptan-3-ol (21)

The same procedure as in Synthesis Example 11 was repeated, except for using n-butyl iodide in place of the n-propyl iodide and 20 g of n-butyl chloride in place of 18 g of the n-propyl chloride to prepare a tetrahydrofuran solution of n-butylmagnesium chloride and replacing the starting 3-[6(S)-2,2,6-trimethylcyclohexan-1-yl]propanal with 3-[6(S)-2,2,6-trimethylcyclohexan-1-yl]propanal, to obtain 9 g of optically active 1-[6(R)-2,2,6-trimethylcyclohexan-1-yl]heptan-3-ol (21).

Boiling point: 109°–110° C./1 mmHg $[\alpha]_D^{25}$: −11.23°

Purity by GC: (21)-Trans: 95.1%; (21)-Cis: 4.9%

Elemental Analysis:

Calcd. (%) C: 79.93; H: 13.42; O: 6.65

Found (%) C: 79.92; H: 13.42; O: 6.66

(21)-Trans

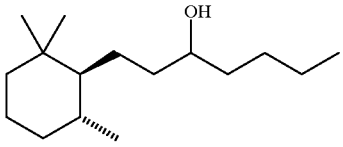

(21)-Cis

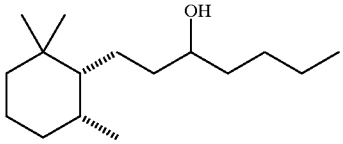

SYNTHESIS EXAMPLE 17

Synthesis of 1-[6(S)-2,2,6-Trimethylcyclohexan-1-yl]-5-methylhexan-3-ol (22)

The same procedure as in Synthesis Example 11 was repeated, except for using isobutyl iodide in place of the n-propyl iodide and isobutyl chloride in place of the n-propyl chloride to prepare a tetrahydrofuran solution of isobutylmagnesium chloride. The resulting concentrated oil (18 g) was subjected to rectification by using a 20 cm Helipack-packed distillation column to obtain 13 g of optically active 1-[6(S)-2,2,6-trimethylcyclohexan-1-yl]-5-methylhexan-3-ol (22).

Boiling point: 103°–104° C./1 mmHg $[\alpha]_D^{25}$: +10.57°

Purity by GC: (22)-Trans: 95.2%; (22)-Cis: 4.8%

Elemental Analysis:

Calcd. (%) C: 79.93; H: 13.42; O: 6.65

Found (%) C: 79.91; H: 13.44; O: 6.65

(22)-Trans

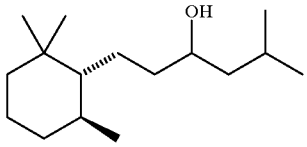

(22)-Cis

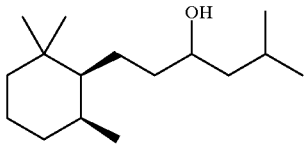

Spectral Data of (22)-Trans:

$^1$HNMR (400 MHz, $CDCl_3$, δ): 0.53 (1H, m), 0.79 (3H, s), 0.87–0.93 (13H), 1.00–1.65 (13H), 1.77 (1H, m), 3.6 (1H, m)

MS m/e: 222 (M-18, 9), 207 (11), 183 (11), 166 (6), 154 (7), 138 (35), 124 (37), 109 (59), 95 (44), 82 (50), 69 (100), 57 (22), 43 (15)

IR $\nu_{max}$ ($cm^{-1}$): 3350, 2950, 2920, 2865, 2840, 1468, 1387, 1368

Spectral Data of (22)-Cis:

MS m/e: 222 (M-18, 13), 207 (33), 183 (4), 166 (4), 151 (3), 138 (37), 123 (67), 109 (33), 95 (62), 69 (100), 55 (26), 43 (15)

SYNTHESIS EXAMPLE 18

Synthesis of 1-[6(R)-2,2,6-Trimethylcyclohexan-1-yl]-5-methylhexan-3-ol (23)

The same procedure as in Synthesis Example 11 was repeated, except for using isobutyl iodide in place of the n-propyl iodide and isobutyl chloride in place of the n-propyl chloride to prepare a tetrahydrofuran solution of isobutylmagnesium chloride and replacing the starting 3-[6(S)-2,2,6-trimethylcyclohexan-1-yl]propanal with 3-[6(S)-2,2,6-trimethylcyclohexan-1-yl]propanal, to obtain 9 g of optically active 1-[6(R)-2,2,6-trimethylcyclohexan-1-yl]-5-methylhexan-3-ol (23).

Boiling point: 103°–104° C./1 mmHg $[\alpha]_D^{25}$: −10.57°

Purity by GC: (23)-Trans: 95.1%; (23)-Cis: 4.9%

Elemental Analysis:

Calcd. (%) C: 79.93; H: 13.42; O: 6.65

Found (%) C: 79.93; H: 13.41; O: 6.66

(23)-Trans

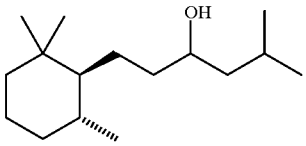

(23)-Cis

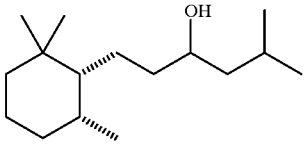

EXAMPLE 1

Odor Evaluation

Odor evaluation was carried out by a panel of 5 specialists on the 6(S)-compound, 6(R)-compound, and racemate of each of the 3-(2,2,6-trimethylcyclohexan-1-yl)propanal derivatives having various alkyl groups as R: as synthesized in the foregoing Synthesis Examples. The results are shown in Tables 1 and 2 below. Standards of rating were as follows.

A . . . Very pleasant and attractive
B . . . Pleasant and makes one to feel a desired to use
C . . . Usable but featureless
D . . . Not so interesting
E . . . Not interesting at all

TABLE 1

| Compound No. | $R^1$ | 6(S)-Compound Odor Character | Compound No. | Rate | 6(R)-Compound Odor Character | Rate |
|---|---|---|---|---|---|---|
| (12), [(13)] | $CH_3$ | slightly floral and orris-like amber fragrance | (13) | B | very faint woody odor | E |
| (14), [(15)] | $C_2H_5$ | highly diffusible, sharp amber fragrance with slight orris-like camphorous side note | (15) | A | faint, slightly amber-like woody odor with a little moldiness | D |
| (16), [(17)] | n-$C_3H_7$ | highly diffusible, sharp amber fragrance with slight orris-like animal note | (17) | A | very faint woody odor with a little moldiness | E |
| (18), [(19)] | i-$C_3H_7$ | relatively powerless and slightly soil-like amber-like woody fragrance | (19) | C | very faint woody odor with a little moldiness | E |
| (20), [(21)] | n-$C_4H_9$ | highly diffusible amber fragrance with slight orris-like side note | (21) | A | faint woody odor with a little moldiness | E |

TABLE 1-continued

| Compound No. | $R^1$ | 6(S)-Compound Odor Character | Compound No. | Rate | 6(R)-Compound Odor Character | Rate |
|---|---|---|---|---|---|---|
| (22), [(23)] | i-$C_4H_9$ | highly diffusible, sharp amber fragrance with slight camphorous side note | (23) | A | faint woody odor with a little moldiness | D |

TABLE 2

| Racemate [Mixture of 6(S)/6(R) = 1/1] | | |
|---|---|---|
| $R^1$ | Odor Character | Rate |
| $CH_3$ | orris-like, woody amber odor with a low floral side note | C |
| $C_2H_5$ | low diffusible, dull, and orris-like woody amber odor | C |
| n-$C_3H_7$ | dull and broadwise spreading woody amber odor | B |
| i-$C_3H_7$ | faint amber odor with soil-like side note | D |
| n-$C_4H_9$ | low diffusible, dull, and faint amber odor | C |
| i-$C_4H_9$ | dull, broadwise spreading, and woody amber odor with slight comphorous side note | B |

EXAMPLE 2

Masking Test of Amino Acid Shampoo

In order to test masking effect on the odor of the base of an amino acid shampoo, a shampoo composition containing 1-[6(S)-2,2,6-trimethylcyclohexan-1-yl]heptane-3-ol or a racemate thereof as shown in Table 3 below was prepared, and the degree of masking was evaluated by a panel of 5 specialists. As a result, the panel judged that Composition A containing the optically active compound smelled pleasantly of amber with the base odor being perfectly masked; Composition B containing the racemate smelled considerably of the base; and the smell of the base was substantially overpowered in Composition C containing the racemate in an amount 8 times that of the optically active compound in Composition A.

TABLE 3

| | Composition A | Composition B | Composition C |
|---|---|---|---|
| Amino acid shampoo | 25 g | 25 g | 25 g |
| 5% Diethylene glycol solution of 1-[6(S)-2,2,6-trimethylcyclohexan-1-yl]heptan-3-ol | 0.1 g | — | — |
| 5% Diethylene glycol solution of racemate [mixture of 6(S)/6(R) = 1/1] | — | 0.2 g | 0.8 g |

EXAMPLE 3

Musk Base

A musk base having the following formulation was prepared, and the 1-[6(S)-2,2,6-trimethylcyclohexan-1-yl]-

5-methylhexan-3-ol as synthesized in Synthesis Example 17 or a racemate thereof [mixture of 6.S()/6(R)=1/1] was compounded therein as shown in Table 4 below. Odor evaluation on the resulting perfumes (B-1, B-2), and B-4) was carried out by a panel of 5 specialists based on the following rating standards. The results are shown in Table 4. As a result of the fragrance test, the panel judged that: B-1 containing the optically active compound and B-4 containing the racemate in an amount 9 times that of the optically active compound in B-1 had an almost equal strength of fragrance, the top note of B-4 being, however, broadwise spreading and lacking sharpness, while B-1 had a well-balanced fragrance with freshness and was preferred to B-4. With respect to B-2, B-3, and B-4, the panel judged that the strength of fragrance was decreasing in the order of B-4>B-3>B-2 and that the preference was also decreasing in the same order.

| Musk Base Formulation: | |
|---|---|
| Coumarin | 60 parts |
| Allyl cyclohexyloxyacetate | 1 part |
| Hydroxycitronellal | 40 parts |
| Geraniol | 40 parts |
| Bourbon geranium oil | 3 parts |
| Piperonal | 20 parts |
| 4-(4-Hydroxy-4-methylpentyl)-3-cyclohexenecarbaldehyde | 40 parts |
| 1-Citronellal | 20 parts |
| Linalool | 20 parts |
| γ-Methyl isomone | 40 parts |
| Ethylene brassylate | 380 parts |
| 10% Dipropylene glycol solution of 4-p-hydroxy-phenylbutan-2-one | 8 parts |
| Phenylethyl alcohol | 40 parts |
| Isobornylcyclohexanol | 108 parts |
| Acetyl cedrene | 80 parts |
| Total: | 900 parts |

TABLE 4

| Composition | Invention | Comparison | | |
|---|---|---|---|---|
| (part): | B-1 | B-2 | B-3 | B-4 |
| Musk base | 900 | 900 | 900 | 900 |
| 1-[6(S)-2,2,6-Trimethyl-cyclohexan-1-yl]-4-methyl-hexan-3-ol | 10 | — | — | — |
| Racemate [mixture of 6(S)/6(R) = 1/1] | — | 20 | 40 | 90 |
| Dipropylene glycol | 90 | 80 | 60 | 10 |
| Total: | 100 | 100 | 100 | 100 |
| Rate | 5 | 2 | 3 | 4 |

Standards of Evaluation:
5 Very pleasant. Very preferable.
4 Fairly pleasant. Preferable.
3 Pleasant. Preferable.
2 Effect of addition was not so perceptible.
1 No effect of addition.

EXAMPLE 4

Perfume Composition for Detergent

A white floral perfume Composition (A) or (B) for detergents having the following formulation was prepared.

| Formulation: | (A) (part) | (B) (part) |
|---|---|---|
| 7-Acetyl-1,1,3,4,4,5-hexamethyl-1,2,3,4-tetrahydronaphthalene | 50 | 50 |
| Ethylene brassylate | 200 | 200 |
| p-Isobutyl α-methylidydro-cinnamic aldehyde | 300 | 300 |
| 2,4-Di-tert-butylcyclohexanone | 100 | 100 |
| γ-Methyl ionone | 30 | 30 |
| Geranium oil | 10 | 10 |
| Tetrahydrollinalool | 50 | 50 |
| Patchouli oil | 10 | 10 |
| Lauryl aldehyde | 5 | 5 |
| Methyl dihydrojasmonate | 100 | 100 |
| Linalool | 45 | 45 |
| Diethyl phthalate | 90 | 80 |
| 1-[6(S)-2,2,6-Trimethylcyclo-hexan-1-yl]-hexan-3-ol | 10 | — |
| Racemate [mixture of 6(S)/6(R) = 1/1] | — | 20 |
| Total: | 1000 | 1000 |

Test of preference was carried out on each of Compositions (A) and (B) by a panel of 5 specialists. As a result, the panel judged that Composition (A) containing the optically active compound was better than Composition (B) because of diffusibility, freshness, and harmony of the fragrance. Further, towels were washed using each of Compositions (A) and (B), and the scent remaining on the laundry was tested by the panel. As a result, the panel judged that the towels washed by using Composition (A) had a stronger and better-balanced scent and were thus preferred.

EXAMPLE 5

Perfume Composition for Shampoo

A green floral and highly preferably perfume composition for shampoo having the following formulation was prepared.

| Formulation: | |
|---|---|
| Ethylene brassylate | 250 parts |
| Musk ketone | 50 parts |
| Methyl dihydrojasmonate | 70 parts |
| p-Isobutyl-α-methyldihydrocinnamic aldehyde | 200 parts |
| 1-Citronellol | 100 parts |
| Eugenol | 20 parts |
| 2-Methyl-4-phenylbutan-2-yl acetate | 50 parts |
| 50% Dipropylene glycol solution of phenylacetaldehyde | 10 parts |
| 2,4-Dimethyl-3-cyclohexenecarbaldehyde | 10 parts |
| Undecylenic aldehyde | 5 parts |
| Lime oil | 20 parts |
| Lemon oil | 40 parts |
| 10% Dipropylene glycol solution of 4-p-hydroxyphenylbutan-2-one | 20 parts |
| Cis-3-hexenyl propionate | 5 parts |
| Tetrahydrolinalool | 50 parts |
| Benzyl salicylate | 80 parts |
| Dipropylene glycol | 10 parts |
| 1-[6(S)-2,2,6-Trimethylcyclohexan-1-yl]-heptan-3-ol | 10 parts |
| Total: | 1000 parts |

EXAMPLE 6

Perfume Composition for Textile Softener

A highly preferable Fougere type perfume composition for textile softeners having the following formulation was prepared.

| Formulation: | |
|---|---|
| Coumarin | 50 parts |
| Ethylene brassylate | 200 parts |
| Patchouli oil | 30 parts |
| Dimethylbenzylmethanal | 100 parts |
| n-Tetradecyl aldehyde | 10 parts |
| 2,4-Di-tert-butylcyclohexanone | 100 parts |
| Benzyl salicylate | 200 parts |
| Lavandin oil | 50 parts |
| α-Amylcinnamic aldehyde | 100 parts |
| Cyclamen aldehyde | 100 parts |
| Acetylcedrene | 50 parts |
| 1-[6(S)-2,2,6-Trimethylcyclohexan-1-yl]-pentan-3-ol | 10 parts |
| Total: | 1000 parts |

EXAMPLE 7

Perfume Composition of Soap

An aldehydic floral bouquet perfume composition (A) or (B) for soaps having he following formulation was prepared.

| Formulation: | (A) (part) | (B) (part) |
|---|---|---|
| Lauryl aldehyde | 10 | 10 |
| Hydroxycitronellal | 50 | 50 |
| Bourbon geranium oil | 10 | 10 |
| Piperonal | 15 | 15 |
| 4-(4-Hydroxy-4-methylpentyl)-3-cyclohexenecarbaldehyde | 60 | 60 |
| 1-Citronellol | 100 | 100 |
| γ-Methyl ionone | 50 | 50 |
| Ethylene brassylate | 390 | 390 |
| Isobornylcyclohexanol | 100 | 100 |
| Acetylcedrene | 80 | 80 |
| Patchouli oil | 20 | 20 |
| 2,4-Dimethyl-3-cyclohexene-carbaldhyde | 5 | 5 |
| Linalool | 90 | 90 |
| 1-[6(S)-2,2,6-Trimethylcyclo-hexan-1-yl]-4-methylhexan-3-ol | 10 | — |
| Racemate [mixture of [6(S)/6(R) = 1/1] | — | 20 |
| Dipropylene glycol | 10 | — |
| Total: | 1000 parts | |

Evaluation test was conducted by 10 panelists on soaps perfumed with 1% of each of Compositions (A) and (B). As a result, 9 out of 10 panelists judged that the fragrance of the soap containing Composition (A) containing the optically active compound was more diffusible and deeper and therefore preferred.

EXAMPLE 8

Liquid Hypochlorite Bleachinc Agent

A liquid hypochlorite bleaching agent having the following formulation was prepared.

| Formulation: | |
|---|---|
| Sodium hypochlorite | 40 parts |
| Sodium polyoxyethylene dodecyl ether sulfate | 20 parts |
| Sodium 2-ethylhexylsulfate | 20 parts |
| Sodium hydroxide | 10 parts |
| Water | 10 parts |
| Total: | 100 parts |

1-[6(S)-2,2,6-Trimethylcyclohexan-1-yl]-pentan-3-ol or a racemate thereof was added to the liquid hypochlorite bleaching solution in an amount of 0.1% or 0.2%, respectively to prepare Composition (A) or (B) having an amber fragrance.

The degree of masking of the odor of the hypochlorite in each of Compositions (A) and (B) was tested by a panel of 5 specialists. As a result, the panel judged that Composition (A) had a fresh amber-like fragrance with no perceptible odor of the hypochlorite, whereas Composition (B) smelled slightly of the hypochlorite.

Further, towels were washed in a washing machine using each of Compositions (A) and (B) as a bleaching agent, and the scent remaining on the laundry was tested by a panel of 5 specialists. As a result, the panel judged that the towels washed by using Composition (A) containing the optically active compound had a pleasant and fresh amber fragrance with no perceptible odor of the hypochlorite, whereas those washed by using Composition (B) containing the racemate smelled slightly of the hypochlorite. Incidentally, the towels washed by using Composition (A) provided bleached (whitened) to the same degree as those washed by using a bleaching agent having the same composition except for the perfume component.

The present invention provides an industrially useful optically active 3-[6(S)-2,2,6-trimethylcyclohexan-1-yl]-propanal derivative and a perfume containing the same as an active ingredient. The optically active 3-[6(S)-2,2,6-trimethylcyclohexan-1-yl]propanal derivative has excellent properties as a perfume, and the perfume containing the same as an active ingredient is useful in broad fields, such as various cosmetics, sanitary goods, pharmaceuticals, etc.

While the invention has been described in detail and with reference to specific embodiments thereof, it will be apparent to one skilled in the art that various changes and modifications can be made therein without departing from the spirit and scope thereof.

What is claimed is:

1. An optically active 3-[6(S)-2,2,6-trimethylcyclohexan-1-yl]propanol derivative represented by formula (I):

(I)

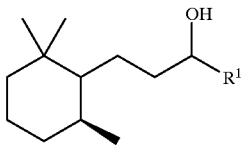

wherein $R^1$ represents a lower alkyl group.

2. A perfume composition comprising an optically active 3-[6(S)-2,2,6-trimethylcyclohexan-1-yl]propanol derivative represented by formula (I):

(I)

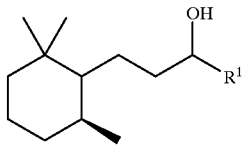

wherein $R^1$ represents a lower alkyl group, as an active ingredient.

3. A perfume composition as in claim 2, wherein said optically active 3-[6(S)-2,2,6-trimethylcyclohexan-1-yl]-propanol derivative represented by formula (I) is present in an amount of from 0.0001 to 50% by weight.

4. A perfume composition as in claim 3, wherein said optically active 3-[6(S)-2,2,6-trimethylcyclohexan-1-yl] propanol derivative represented by formula (I) is present in an amount of from 0.001 to 20% by weight.

5. A perfume composition comprising a compound represented by formula (I) as an active ingredient, wherein 95% or more of said compound represented by formula (I) is in the trans-form:

an optically active 3-[6(S)-2,2,6-trimethyl-cyclohexan-1-yl]propanol derivative represented by formula (I):

(I)

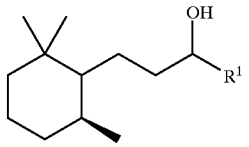

wherein $R^1$ represents a lower alkyl group.

6. A perfume composition comprising a compound represented by formula (I) as an active ingredient, wherein 95% or more of said compound represented by formula (I) is in the trans form and has an optical purity of 98% ee or more:

an optically active 3-[6(S)-2,2,6-trimethyl-cyclohexane-1-yl]propanol derivative represented by formula (I):

(I)

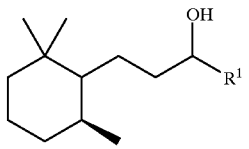

wherein $R^1$ represents a lower alkyl group.

7. A perfume composition comprising a compound represented by formula (I) as an active ingredient, wherein 95% or more of said compound represented by formula 91) is in the trans form:

an optically active 3-[6(S)-2,2,6-trimethyl-cyclohexan-1-yl]propanol derivative represented by formula (I):

(I)

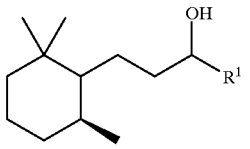

wherein $R^1$ represents an ethyl group, an n-propyl group, an n-butyl group or an isobutyl group.

8. A perfume composition comprising a compound represented by formula (I) as an active ingredient, wherein 95% or more of said compound represented by formula (I) is in the trans form and has an optical purity of 98% ee:

an optically active 3-[6(S)-2,2,6-trimethylcyclohexan-1-yl]propanol derivative represented by formula (I):

(I)

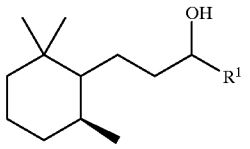

wherein $R^1$ represents an ethyl group, an n-propyl group, an n-butyl group or an isobutyl group.

9. A perfume composition comprising a compound represented by formula (I) as an active ingredient, wherein 95% or more of said compound represented by formula (I) is in the trans form and is obtained from 1-methoxycitronellal having an optical purity of 98% ee:

an optically active 3-[6(S)-2,2,6-trimethyl-cyclohexan-1-yl]propanol derivative represented by formula (I):

(I)

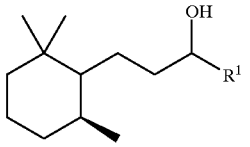

wherein $R^1$ represents a lower alkyl group.

*10. A perfume composition comprising a mixture of two compounds represented by formula (I) as an active ingredient, wherein 95% or more of said compounds represented by formula (I) are in the trans form with the cis form being present in an amount in combination with said 95% or more of said trans form to impart an amber fragrance to said perfume composition, said compound represented by formula (I) having an optical purity of 98% ee or more,*

(I)

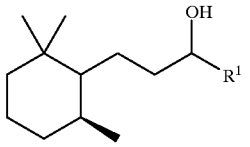

*wherein 5% or less of said compounds represented by formula (I) are in the cis form and $R^1$ represents an ethyl, n-propyl, n-butyl or isobutyl group.*

*11. A perfume composition as claimed in claim 10, wherein the ratio of the compounds having the trans form and the compounds having the cis form ranges from 95/5–95.3/4.7 by weight.*

*12. The perfume composition of claim 10 wherein $R^1$ is ethyl.*

*13. The perfume composition of claim 10 wherein $R^1$ is n-propyl.*

*14. The perfume composition of claim 10 wherein $R^1$ is isobutyl.*

* * * * *